United States Patent [19]

Lyle

[11] Patent Number: 5,061,286
[45] Date of Patent: Oct. 29, 1991

[54] OSTEOPROSTHETIC IMPLANT

[75] Inventor: John W. Lyle, Belmar, N.J.

[73] Assignee: Osteotech, Inc., Shrewsbury, N.J.

[21] Appl. No.: 395,783

[22] Filed: Aug. 18, 1989

[51] Int. Cl.$^5$ .............................................. A61F 2/28
[52] U.S. Cl. ........................................ 623/16; 623/66; 623/23
[58] Field of Search .................. 623/1, 11, 12, 16, 18, 623/20, 22, 23, 66; 433/199, 201, 180, 201.1, 212.1, 222.1, 226; 606/76

[56] References Cited

U.S. PATENT DOCUMENTS

| | | |
|---|---|---|
| 3,808,606 | 5/1974 | Tronzo . |
| 3,918,100 | 11/1975 | Shaw et al. . |
| 3,986,212 | 10/1976 | Sauer . |
| 4,159,358 | 6/1979 | Hench et al. . |
| 4,164,794 | 8/1979 | Spector et al. . |
| 4,168,326 | 9/1979 | Broemer et al. . |
| 4,180,646 | 12/1979 | Choi et al. . |
| 4,202,055 | 5/1980 | Reiner et al. . |
| 4,347,234 | 8/1982 | Wahlig et al. ........................ 623/16 |
| 4,351,069 | 9/1982 | Ballintyn et al. . |
| 4,365,356 | 12/1982 | Broemer et al. . |
| 4,472,840 | 9/1984 | Jefferies ............................... 623/16 |
| 4,485,097 | 11/1984 | Bell . |
| 4,491,987 | 1/1985 | Park . |
| 4,652,459 | 3/1987 | Englehardt . |
| 4,678,470 | 7/1987 | Nashef et al. . |
| 4,702,930 | 10/1987 | Heide et al. . |
| 4,705,694 | 11/1987 | Buttazzoni et al. . |
| 4,713,076 | 12/1987 | Draenert . |
| 4,743,259 | 5/1988 | Bolander et al. . |
| 4,778,469 | 10/1988 | Lin et al. . |
| 4,826,945 | 5/1989 | Cohn et al. . |

FOREIGN PATENT DOCUMENTS 2620890 11/1977 Fed. Rep. of Germany ........ 623/16

OTHER PUBLICATIONS

[Mellonig], "Decalified Freeze-Dried Bone Allograft as an Implant Material In Human Periodontal Defects", the International Journal of Periodontics and Restorative Dentistry, pp. 41–55 (Jun. 1984).

Kaban et al., "Treatment of Jaw Defects with Demineralized Bone Implants", Journal of Oral and Maxillofacial Surgery.

Bolander et al., "The Use of Demineralized Bone Matrix in the Repair of Segmental Defects", The Journal of Bone & Joint Surgery, vol. 68-A, No. 8, pp. 1264–1273.

Glowacki et al., "Demineralized Bone Implants", Symposium on Horizons in Plastic Surgery, vol. 12, No. 2, pp. 233–241 (1985).

Gepstein et al., "Bridging Large Defects in Bone by Demineralized Bone Matrix in the Form of a Powder", The Journal of Bone and Joint Surgery, vol. 69-A, No. 7, pp. 984–991 (1987).

McLaughlin et al., "Enhancement of Bone Ingrowth by the Use of Bone Matrix as a Biologic Cement", Clinical Orthopaedics and Related Research, No. 183, pp. 255–261 (Mar. 1984).

Primary Examiner—David J. Isabella
Attorney, Agent, or Firm—Dilworth & Barrese

[57] ABSTRACT

At least a portion of the surface of an osteoprosthetic implant is provided with demineralized bone powder adhering thereto. Sorption of the bone particles is accompanied by rapid and deep bone in-growth which firmly anchors the prosthesis to the host bone repair site.

19 Claims, 1 Drawing Sheet

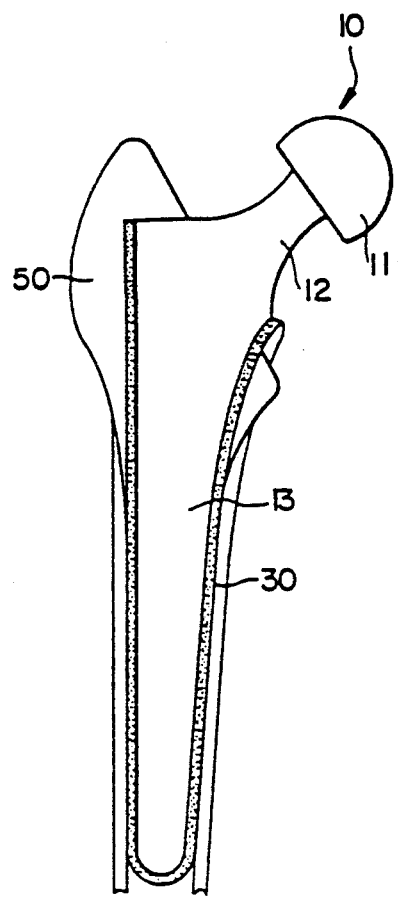
FIG. 1
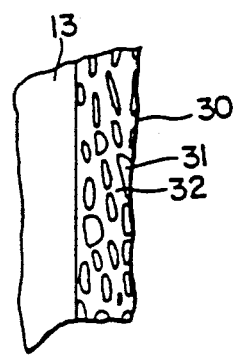
FIG. 2
FIG. 3
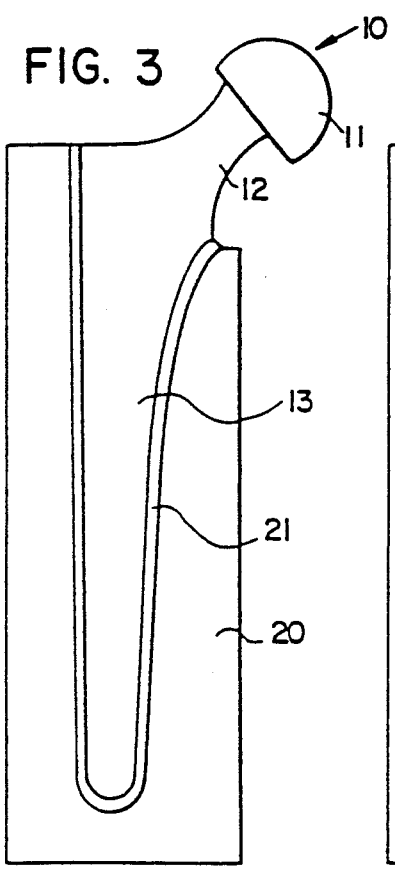
FIG. 4
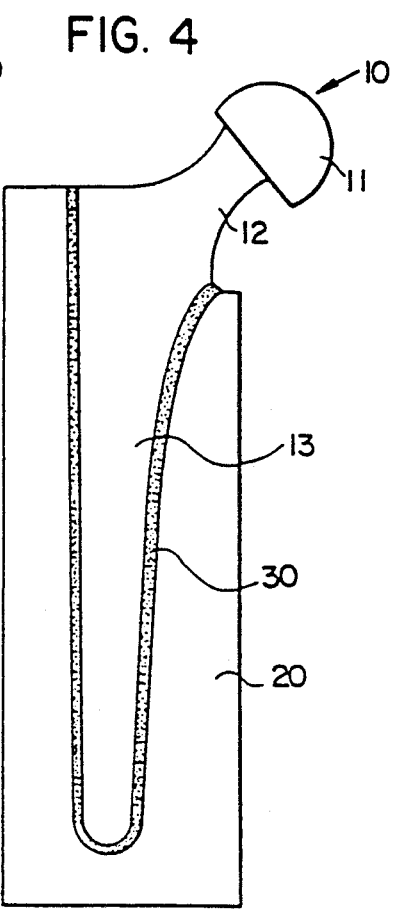
FIG. 5
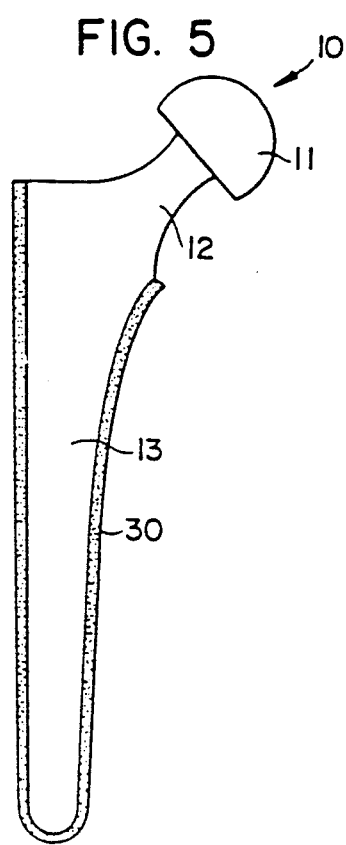

OSTEOPROSTHETIC IMPLANT

BACKGROUND OF THE INVENTION

This invention relates to implantable osteoprosthetic devices and, more particularly, to such prostheses formed as a composite which includes a bone growth-inducing layer or coating.

Many osteoprosthetic devices, e.g., those used in the reconstruction of the hip joint, are joined to the skeletal system by impacting an anchorage component within the intramedullary canal of the bone or by mechanically fixing the device by means of a bone cement such as a polymethylmethacrylate. However, these methods are not entirely satisfactory due to the tendency of the devices to loosen upon impact or as a result of use over a long period of time.

Tissue ingrowth has also been used in attempts to anchor osteoprosthetic devices in place. In this method, the prosthesis is provided with a porous surface which is intended to foster bone ingrowth and serve as an attachment site for the new bone tissue. The tissue ingrowth approach to anchoring a prosthesis has been adopted for a variety of endoprosthetic devices.

U.S. Pat. No. 3,986,212 describes a porous polymeric coating for bone fixation by tissue ingrowth. The porous polymeric materials which are indicated to be useful are those having a specified density and interconnected pores of a specific average pore diameter. Among the polymeric materials disclosed are high density polyethylene and polypropylene or mixtures thereof having certain critical parameters. It is also indicated that the coatings can be mechanically interlocked or chemically bonded to the device.

Similarly, in U.S. Pat. No. 4,164,794, an osteoprosthetic device is coated with a porous thermoplastic material of particular properties which is said to be compatible with, and conducive for, the ingrowth of cancellous and cortical bone specules.

The anchorage component of the endoprosthetic device described in U.S. Pat. No. 4,202,055 possesses a non-porous polymeric coating in which particles of ceramic have been incorporated. Upon resorption of the ceramic particles, a polymer structure with continuous pores is formed which is penetrated by newly formed bone.

In accordance with U.S. Pat. No. 4,713,076, the anchorage component of an osteoprosthetic device possesses a completely resorbable coating which is said to enable fast and deep ingrowth of new bone tissue and anchor the implant within the bone. The coating composition is made up of a calcium compound, e.g., tricalcium phosphate or apatite (hydroxyl apatite) provided in the form of highly porous spherical particles which are embedded in a resorbable, biologically compatible binding agent such as a polyamino acid, polylactate, polyglycolate, co-condensates of these substances, gelatin or collagen.

Other types of coated osteoprosthetic devices are described in U.S. Pat. Nos. 3,808,606; 4,159,358; 4,168,326; 4,351,069; 4,365,356; 4,491,987; 4,652,459; 4,702,930; and, 4,705,694.

The use of pulverized exogenous bone growth material, e.g., derived from demineralized allogenic or xenogenic bone, is also known. See, in this regard, the disclosures of U.S. Pat. Nos. 4,485,097; 4,678,470 and 4,743,259; Bolander et al., "The Use of Demineralized Bone Matrix in the Repair of Segmental Defects", *The Journal of Bone and Joint Surgery*, Vol. 68-A, No. 8, pp. 1264–1273; Glowacki et al., "Demineralized Bone Implants", *Symposium on Horizons in Plastic Surgery*, Vol. 12, No. 2, pp. 233–241 (1985); Gepstein et al., "Bridging Large Defects in Bone by Demineralized Bone Matrix in the Form of a Powder", *The Journal of Bone and Joint Surgery*, Vol. 69-A, No. 7, pp. 984–991 (1987); [Mellonig], "Decalcified Freeze-Dried Bone Allograft as an Implant Material in Human Periodontal Defects", *The International Journal of Periodontics and Restorative Dentistry*, pp. 41–55 (June, 1984): and, Kaban et al., "Treatment of Jaw Defects with Demineralized Bone Implants", *Journal of Oral and Maxillofacial Surgery*, However, there is no suggestion in any of these prior disclosures of combining an osteoprosthetic component with a bone growth-inducing component based on a powdered bone material.

SUMMARY OF THE INVENTION

It is an object of the invention to provide an osteoprosthetic implant possessing a bone growth-inducing component.

It is a particular object of the invention to provide an endoprosthesis, e.g., a hip joint replacement, in which at least a portion of the surface of the endoprosthesis possesses an osteogenic coating or layer of demineralized bone powder, optionally distributed within a biocompatible, non-bioerodable binding agent or matrix.

In keeping with these and other objects of the invention, at least a portion of the surface of an osteoprosthetic implant possesses a bone powder component adherently distributed thereon. As the bone powder undergoes gradual resorption, new bone ingrowth takes the place of the resorbed bone particles thereby providing a firm union between the prosthesis and pre-existing bone tissue. Unlike the non-osteogenic particles contained in known prosthetic coatings, e.g., those disclosed in U.S. Pat. No. 4,202,055 discussed supra, the demineralized bone powder which is applied to the endoprosthesis of this invention provides a significant osteogenic effect which significantly accelerates new bone ingrowth.

BRIEF DESCRIPTION OF THE DRAWINGS

In the accompanying drawings in which like numerals refer to like elements:

FIG. 1 is a schematic illustration of a hip joint prosthesis possessing a bone growth-inducing coating in accordance with the invention, the coated prosthesis being set in place within the intramedullary canal of the femur;

FIG. 2 shows an enlarged section of the bone growth-inducing coating as applied to the hip joint endoprosthesis of FIG. 1; and, FIGS. 3 to 5 are schematic illustrations in side profile view of one method of applying a bone growth-inducing coating to the hip joint prosthesis of FIG. 1.

DESCRIPTION OF THE PREFERRED EMBODIMENTS

The demineralized pulverized or powdered bone which is incorporated in the osteogenic layer or coating herein is a known type of material and is prepared in accordance with known procedures. The expressions "pulverized bone", "powdered bone" and "bone powder" as used herein shall be understood to include bone particles of a wide range of average particle size ranging from relatively fine powders to coarse grains and even larger chips. So, for example, the bone powder used in this invention can range in average particle size from about 0.1 to about 1.2 cm and preferably from 0.2 to 1 cm. The bone powder can be obtained from a variety of sources including human allograft tissue, xenograft tissue and can be cancellous and/or cortical bone tissue.

In a preferred bone demineralization procedure, the bone is first pulverized to the desired average particle size followed by defatting/disinfecting and acid demineralization treatments. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably 70% alcohol. Following defatting, the bone undergoes a pH controlled immersion in an acid, such as 0.6N hydrochloric acid, for about 3 hours to effect demineralization. Other acids which can be employed in the same or other concentrations include other inorganic as well as organic acids such as peracetic acid. After acid treatment, the bone powder is rinsed with water for injection, buffered with a buffering agent such as 0.1M sodium phosphate solution to a final controlled pH and then finally rinsed with water for injection to remove residual amounts of hydrochloric acid and sodium phosphate. The demineralized bone powder can be used immediately for application to the osteoprosthetic device of this invention or it can be stored under aseptic conditions, advantageously in a freeze-dried state, prior to such application.

If desired, the bone powder can be modified in one or more ways, e.g., the porosity of the bone powder can be increased and/or the bone powder can be treated with one or more modifying agents, e.g., glutaraldehyde, as disclosed in U.S. Pat. No. 4,678,470. Another optional treatment involves the augmentation of the bone protein content of the powdered bone employing the procedure of U.S. Pat. No. 4,743,259. Any of a variety of substances can be introduced into the bone particles, e.g., by soaking or immersing the bone particles in a solution of the desired substance(s) followed by drying of the bone particles. Substances which can be readily incorporated in the bone particles in this or any other suitable manner include antiviral drugs, e.g., those suitable for preventing transmission of acquired immune deficiency syndrome (AIDS); antimicrobials and/or antibiotics such as erythromycin, bacitracin, neomycin, penicillin, polymyxin B, tetracyclines, viomycin, chloromycetin and streptomycins, cefazolin, ampicillin, tobramycin, clindamycin and gentamicin, etc.; amino acids, peptides, vitamins, inorganic elements, NAD and/or other nutrients; hormones; endocrine tissue or tissue fragments; synthesizers; enzymes such as collagenase, peptidases, oxidases, etc.; polymer-cell scaffolds with parenchymal cells; angiogenic drugs and polymeric carriers containing such drugs; collagen lattices; biocompatible surface active agents; antigenic agents; cytoskeletal agents; biologically active components such as bone morphogenetic proteins (BMPs), transforming growth factor (TCF-beta), insulin-like growth factor (IGD-1); mesenchymal elements; bone digestors; antitumor agents; cellular attractants and attachment agents; immunosuppressants; permeation enhancers, e.g., fatty acid esters such as the laurate, myristate and stearate monoesters of polyethylene glycol, enamine derivatives, alpha-keto aldehydes, etc.; and, nucleic acids. The amounts of optionally added substances can vary widely with optimum levels being readily determined in a specific case by routine experimentation.

The adherent bone powder component of the osteoprosthesis herein can be applied to the surface of the prosthetic device in any one of several ways. Thus, e.g., the bone particles and/or the surface of the prosthesis can be provided with a suitable cement or adhesive such as any of those known in the art, e.g., cyanoacrylate, silicones, hot melt adhesives, cellulosic binders, with subsequent contact of the bone particles with the prosthesis, e.g., by spraying, brushing, etc., being sufficient to adhere the bone particles to the surface of the prosthesis or any preselected area(s) or portion(s) of the surface. Another useful procedure involves applying a charge to the prosthesis and an opposite charge to the bone powder, i.e., the technique of electrostatic precipitation, with the result that the bone powder is attracted to, and tenaciously adheres to, the surface of the prosthesis. Any of these application techniques can be repeated one or more times to build up a relatively thick layer of adherent bone powder on the surface of the prosthesis, e.g., a thickness of bone powder ranging from approximately the average particle size of the bone powder to twenty times or more such average particle size.

In a particular embodiment of the invention, the bone powder is applied to the prosthetic device as part of a coating or layer in which the bone particles are incorporated within a biocompatible, non-bioerodable binding agent. The term "non-bioerodable" is used herein to refer to those materials which are not readily or quickly resorbed by the body (i.e., biosorbed) if at all but does not exclude materials which may undergo some resorption after an extended period of residence in the body, e.g., after two years or so. Useful biocompatible, non-bioerodable materials which can be used in the preparation of the osteogenic prosthetic coating or layer include inorganic materials such as enamels and enamel-like materials, e.g., those disclosed in U.S. Pat. Nos. 4,168,326 and 4,365,356, the contents of which are incorporated by reference herein, and organic materials such as porous high density polyethylenes, polypropylenes, polysulfones, polyphenylenesulfides, polyacetals, thermoplastic polyesters, polyamides, polyamideimides, thermoplastic polyimides, polyaryletherketones, polyarylethernitriles, aromatic polyhydroxy-ethers, polyacrylates, polymethacrylates, polyacrylonitriles, polyphenyleneoxides, and so forth, described inter alia, in U.S. Pat. Nos. 3,986,212; 4,164,794; 4,202,055; and, 4,351,069, the contents of which are incorporated by reference herein. The amount of bone powder which can be incorporated into the binding agent to provide the osteogenic layer or coating of this invention can also vary widely with amounts of from about 5 to about 80 weight percent, and preferably from about 20 to about 60 weight percent, being entirely suitable in most cases.

In addition to, or in lieu of, incorporating any of the aforementioned optionally added substances in the bone powder, such substance(s) can also be incorporated in the binding agent. For example, the binding agent can contain at least one additional ingredient selected from the group consisting of reinforcing fiber and reinforcing particle.

Although the invention will now be illustrated in connection with a hip joint endoprosthesis, it is to be understood that the invention can be practiced with any type of bone implant or replacement, e.g., one used in dental or maxillofacial reconstruction.

As shown in FIGS. 1-5, femoral component 10 of a known type of hip joint prosthesis is fabricated from any of a variety of bioengineering materials such as metal, ceramic, polymers and their composites, and the like. The prosthesis includes a head 11, a neck 12 and a stem 13 which serves as an anchorage to secure the implant within the intramedullary canal of femur 50. In one embodiment of the invention, binder component 32 of osteogenic layer 30, selected to be an enamel or enamel-like material, is applied to the surface of stem 13 employing enamelling procedures which are themselves well known in the art, e.g., the wet process, the dry process, the electrophoretic process, the flame-spraying process, the plasma-spraying process, and so on. The binder can be applied as a single layer or in several layers which can be of the same or different composition. Bone powder particles 31 are incorporated into binder 32 while the latter is still in the soft condition, e.g., by spraying the bone particles onto the surface of the binder employing an air blast. The depth to which the individual particles of bone powder 31 penetrate into the enamel binder will depend on the viscosity of said layer and on the pressure of the air blast directing particles 31 against the surface of the binder. The thickness of osteogenic layer 30 is not especially critical. Average thicknesses of from about 1 to about 50 mils and advantageously from about 10 to about 40 mils generally provide satisfactory results.

Of course, the bone particles 31 can be introduced into and/or upon binder 32 by means of other processes, for instance, by pressing the particles into the enamelled layer by means of a mold fitting the prosthesis working piece.

When binder component 32 is selected to be a synthetic organic polymer such as any of those previously mentioned, one convenient procedure for applying the osteogenic coating to the prosthesis is illustrated in FIGS. 3-5. In accordance with this procedure, a plasticized mass of binding agent is first prepared with the demineralized bone being substantially uniformly incorporated therein. Thus, for example, where the binding agent is a thermoplastic polyester, a quantity of the resin is plasticized to a paste-like consistency utilizing a suitable solvent such as benzene, toluene, xylene, and the like, followed by uniform incorporation of the bone powder therein. The fluent mass of material can be applied to the surface of stem 13 in excess and following placement of the prosthesis in the mold and closing of the mold, excess material is expelled from the mold. Alternatively, the uncoated prosthesis is positioned within mold half 20, the other mold half is locked in place and a quantity of the plasticized osteogenic coating material is injected just to the point of excess within space 21. Following formation of osteogenic layer 30 about stem 13 as shown in FIG. 4, the prosthesis is removed from the mold and, following evaporation of the plasticizing solvent, the coated prosthesis, shown in FIG. 5, is now ready for sterilization and aseptic packaging.

In yet another technique for applying osteogenic coating 30 to the anchorage component of endoprosthesis 10, the binding agent is provided as a fine powder, e.g., of an average particle size approximately that of the demineralized bone powder, the latter being uniformly mixed with the binding agent powder to provide a dry, readily flowing powder mixture which is then introduced to excess within space 21 of mold 20. Thereafter, heating of the powder mixture to a temperature at which it forms a self-supporting adherent coating, e.g., a temperature which is sufficient to weld or melt the binding agent particles into a unitary mass, followed by cooling to ambient temperature provides the coated prosthetic device of this invention.

Osteogenic coating 30 can also be applied to the surface of stem 13 by first applying a solvent solution of binding agent to the stem and, following partial evaporation of the solvent to provide a tacky coating, demineralized bone powder is contacted with, and retained by, the binding agent. This procedure can be repeated several times to build the coating up to a predetermined thickness. Complete evaporation of solvent results in the fully formed osteogenic coating.

The thickness of the osteogenic coating or layer is not especially critical. Average thicknesses of from about 1 to about 50 mils and advantageously from about 10 to about 40 mils generally provide satisfactory results.

If desired, the surface of the prosthesis, e.g., stem 13, which is to receive the osteogenic coating or layer can be subjected to one or more preparative treatments in order to enhance the adhesion of the osteogenic coating or layer thereto i.e., prior to application of the bone powder and/or the binding agent thereto. For example, the surface of the prosthesis can be provided with an adhesion-promoting pattern formed as described in U.S. Pat. No. 4,778,469, or an adhesion-promoting roughened surface texture as described in U.S. Pat. No. 4,159,358.

If desired, the surface area of osteogenic coating 30 can be increased to expose a greater surface area of bone particles contained therein to tissue fluids, cells, cell components, etc. and/or to accelerate the dissemination of optional coating components such as any of those previously mentioned into the surrounding environment. The increased surface area can be achieved by modifying the surface of the coating employing any one of a variety of known and conventional techniques including texturizing, etching, embossing, sintering, introducing voids or pores into the layer, etc.

The following example is illustrative of the prosthetic implant and osteogenic coating composition of this invention.

EXAMPLE

A. Preparation of Demineralized Cortical Bone Powder

A quantity of cortical bone which has been pulverized and sieved to an average particle size of from about 100 to about 300 microns is introduced into a reactor which is then sealed. A 70% ethanol solution at the rate of 30 milliliters per gram of bone is introduced into the reactor followed by agitation for 1 hour (Bolander et al., *Journal of Bone and Joint Surgery*, Vol. 68-A, No. 8 (Oct. 1986)) to effect defatting and disinfecting of the bone powder. Following drainage of the ethanol, a 0.6N solution of HCl at a rate of 50 ml per gram of bone is introduced into the reactor (Bolander et al., ibid.), the reaction proceeding for 3 hours (Glowackie, *AATB*

Workshop, 11th Annual meeting (1987)). Following drainage of the HCl, the bone is covered and rinsed three times with water for injection (WFI) with the WFI being replaced at 5 minute intervals. Following drainage of the WFI, the bone is completely covered with 0.1M sodium phosphate, a procedure which is repeated until the pH of the solution falls between 6.8 and 7.4. The rinsing procedure with WFI is repeated to provide demineralized cortical bone powder ready for application herein.

B. Application of Demineralized Cortical Bone Powder to The Stem of a Hip Joint Endoprosthesis A binding agent solution of polybutylene terephthalate (PBT) in m-cresol is prepared by dissolving 20 weight percent PBT in the form of a powder in 80 weight percent m-cresol. The stem of a hip joint prosthesis is dipped in the binding agent solution, the solution is dried to a tacky consistency and bone powder is dusted onto the surface of the binding agent to which it readily adheres. The procedure is repeated several times to build up an osteogenic layer of about 2–3 millimeters average thickness and containing from about 40 to about 50 weight percent demineralized cortical bone powder on the surface of the stem of the prosthesis. Following complete evaporation of solvent in a drying chamber, the coated prosthesis is sterilized and packaged employing known and conventional procedures.

What is claimed is:

1. An osteoprosthetic device possessing an osteogenic coating composition adhering to at least a portion of a surface thereof,
    wherein said coating composition consists essentially of demineralized bone powder substantially uniformly distributed within a biocompatible, non-bioerodible binding agent whereby as the demineralized bone powder undergoes gradual resorption, new bone ingrowth is induced and replaces the resorbed demineralized bone powder to provide a firm connection between the prosthesis and the pre-existing bone tissue.

2. The osteoprosthetic device of claim 1 wherein the binding agent is an enamel.

3. The osteoprosthetic device of claim 1 wherein the demineralized bone powder is derived from cortical bone.

4. The osteoprosthetic device of claim 1 wherein the binding agent contains from about 5 to about 80 weight percent demineralized bone powder.

5. The osteoprosthetic device of claim 1 wherein the binding agent contains from about 20 to about 60 weight percent demineralized bone powder.

6. The osteoprosthetic device of claim 1 wherein the binding agent is an enamel-like material.

7. The osteoprosthetic device of claim 1 wherein the binding agent is a synthetic organic polymer.

8. The osteoprosthetic device of claim 1 wherein the polymer is selected from the group consisting of porous high density polyethylene, polypropylene, polysulfone, polyphenylenesulfide, polyacetal, thermoplastic polyester, polyamide, polyamideimide, thermoplastic polyimide, polyaryletherketone, polyarylethernitrile, aromatic polyhydroxyether, polyacrylate, polymethacrylate, polyacrylonitrile, and polyphenyleneoxide.

9. The osteoprosthetic device of claim 1 wherein the binding agent contains at least one additional ingredient selected from the group consisting of reinforcing fiber and reinforcing particle.

10. The osteoprosthetic device of claim 1 wherein the bone powder contains at least one additional ingredient selected from the group consisting of antiviral agent, antimicrobial agent, antibiotic agent, amino acid, peptide, vitamin, inorganic element, NAD, hormone, endocrine tissue, synthesizer, enzyme, polymer-cell scaffolding agent with parenchymal cells, angiogenic drug, polymeric drug carrier, collagen lattice, surface active agent, antigenic agent, cytoskeletal agent, biologically active component, mesenchymal agent, bone digestor, antitumor agent, cellular attractant, cellular attachment agent, immunosuppressant, nucleic acid and penetration enhancer.

11. The osteoprosthetic device of claim 1 wherein the binding agent contains at least one additional ingredient selected from the group consisting of antiviral agent, antimicrobial agent, antibiotic agent, amino acid, peptide, vitamin, inorganic element, NAD, hormone, endocrine tissue, synthesizer, enzyme, polymer-cell scaffolding agent with parenchymal cells, angiogenic drug, polymeric drug carrier, collagen lattice, surface active agent, antigenic agent, cytoskeletal agent, biologically active component, mesenchymal agent, bone digestor, antitumor agent, cellular attractant, cellular attachment agent, immunosuppressant, nucleic acid and penetration enhancer.

12. The osteoprosthetic device of claim 1 in which the thickness of the coating is from about 1 to about 50 mils.

13. The osteoprosthetic device of claim 1 in which the thickness of the coating is from about 10 to about 40 mils.

14. The osteoprosthetic device of claim 1 provided with an adhesion-promoting surface prior to application of the bone powder thereto.

15. The osteoprosthetic device of claim 1 provided with an adhesion-promoting surface prior to application of the binding agent thereto.

16. The osteoprosthetic device of claim 1 in which a surface of the coating is modified to increase its surface area.

17. The osteoprosthetic device of claim 1 wherein the device is structured and formed as an orthopedic, dental or maxillofacial prosthesis.

18. An osteoprosthetic device possessing an osteogenic coating composition adhering to at least a portion of a surface thereof,
    the coating composition comprising demineralized bone powder substantially uniformly distributed within a biocompatible, non-bioerodible binding agent.
    wherein the average particle size of the demineralized bone powder is from about 0.1 to about 1.2 cm whereby as the demineralized bone powder undergoes gradual resorption, new bone ingrowth is induced and replaces the resorbed diemineralized bone powder to provide a firm connection between the prosthesis and the pre-existing bone tissue.

19. An osteoprosthetic device possessing an osteogenic coating composition adhering to at least a portion of a surface thereof,
    the coating composition comprising demineralized bone powder substantially uniformly distributed within a biocompatible, non-bioerodible binding agent,
    wherein the average particle size of the demineralized bone powder is from about 0.2 to about 1 cm whereby as the demineralized bone powder undergoes gradual resorption, new bone ingrowth is induced and replaces the resorbed demineralized bone powder to provide a firm connection between the prosthesis and the pre-existing bone tissue.

* * * * *